United States Patent
Kwon et al.

(10) Patent No.: US 11,779,211 B2
(45) Date of Patent: Oct. 10, 2023

(54) FLUORESCEIN FLUORESCENT FUNDUS ANGIOGRAPHY DEVICE EMPLOYING POLARIZING BEAM SPLITTER AND LINEAR POLARIZING FILTER

(71) Applicant: AIINSIGHT INC., Busan (KR)

(72) Inventors: Hanjo Kwon, Busan (KR); Keun Heung Park, Busan (KR)

(73) Assignee: AIINSIGHT INC., Busan (KR)

( * ) Notice: Subject to any disclaimer, the term of this patent is extended or adjusted under 35 U.S.C. 154(b) by 617 days.

(21) Appl. No.: 16/980,135

(22) PCT Filed: Mar. 13, 2019

(86) PCT No.: PCT/KR2019/002869
§ 371 (c)(1),
(2) Date: Sep. 11, 2020

(87) PCT Pub. No.: WO2019/177350
PCT Pub. Date: Sep. 19, 2019

(65) Prior Publication Data
US 2021/0244275 A1  Aug. 12, 2021

(30) Foreign Application Priority Data

Mar. 13, 2018 (KR) ........................ 10-2018-0029018

(51) Int. Cl.
*A61B 3/12* (2006.01)
*G02B 27/28* (2006.01)

(52) U.S. Cl.
CPC .......... *A61B 3/1241* (2013.01); *G02B 27/283* (2013.01); *G02B 27/288* (2013.01)

(58) Field of Classification Search
CPC ... A61B 3/1241; G02B 27/283; G02B 27/288
USPC ......................................................... 351/206
See application file for complete search history.

(56) References Cited

U.S. PATENT DOCUMENTS 8,705,046 B2 * 4/2014 Yun ..................... G01B 9/02081
356/497
2006/0146284 A1 7/2006 Collins et al.

FOREIGN PATENT DOCUMENTS

| JP | 2017-512992 A | 5/2017 |
| JP | 2017-143994 A | 8/2017 |
| KR | 10-2003-0031450 A | 4/2003 |
| KR | 10-2013-0099113 A | 9/2013 |

OTHER PUBLICATIONS

International Search Report for PCT/KR2019/002869 dated Jul. 9, 2019 from Korean Intellectual Property Office.

* cited by examiner

Primary Examiner — Wyatt A Stoffa
Assistant Examiner — Grant A Gagnon
(74) Attorney, Agent, or Firm — Paratus Law Group, PLLC

(57) ABSTRACT

Disclosed is a fluorescent fundus camera which is one kind of ophthalmological diagnostic equipment, using a blue excitation light beam when a contrast medium appears in the retinal vessels. When an abnormal blood vessel is present, the contrast medium leaks into the retina or appears as color in tissues surrounding the retina, and the presence of damage to the retina and the appearance of abnormal neovascularization can be found.

5 Claims, 5 Drawing Sheets

FLUORESCEIN FLUORESCENT FUNDUS ANGIOGRAPHY DEVICE EMPLOYING POLARIZING BEAM SPLITTER AND LINEAR POLARIZING FILTER

CROSS REFERENCE TO PRIOR APPLICATION

This application is a National Stage Patent Application of PCT International Patent Application No. PCT/KR2019/002869 (filed on Mar. 13, 2019) under 35 U.S.C. § 371, which claims priority to Korean Patent Application No. 10-2018-0029018 (filed on Mar. 13, 2018), which are all hereby incorporated by reference in their entirety.

BACKGROUND

The present invention relates to a fluorescent fundus camera which is a type of a fluorescent fundus angiography camera which is one kind of ophthalmological diagnostic equipment and by which, when a contrast medium reaches retinal blood vessels and, after the contrast medium propagating along the retinal blood vessels is irradiated with a blue excitation light beam, a green light beam which is emitted by the contrast medium is detected. When an abnormal blood vessel is present, the contrast medium leaks into a peripheral space of the retina or appears as color in tissues surrounding the retina, and the presence of damage to the retina and the appearance of abnormal neovascularization may be found.

The present invention relates to a fluorescent fundus camera which is a type of a fluorescent fundus angiography camera which is one kind of ophthalmological diagnostic equipment. Fluorescent fundus angiography is a method of continuously photographing, after injecting a contrast medium, the retinal fundus, which is a tissue located at the back of the eyeball to sense light, using a fundus camera. When fluorescein is injected intravenously into an arm and the contrast medium circulates throughout the body and appears in the retinal blood vessels, an interior of the eye is continuously photographed through a fluorescent fundus camera using blue excitation light. In this case, when an abnormal blood vessel is present, the contrast medium leaks into a peripheral space of the retina or exhibits by appears as color in tissues surrounding the retina, and the fluorescent fundus camera is ophthalmological diagnostic equipment which is capable of finding the presence of damage to the retina and the appearance of abnormal angiogenesis.

Fluorescein, which is one kind of fluorescent contrast medium, is a fluorescent material which emits green waves having a wavelength ranging from 500 nm to 600 nm when absorbing blue waves having a wavelength ranging from 470 nm to 510 nm. At a typical test concentration, it is known that a maximum absorption wavelength of the fluorescein dissolved in plasma is 480 nm and a maximum emission wavelength is 525 nm. The core of a general camera-type fluorescent fundus angiography device is formed by adding a broadband white light source, an excitation filter, and a blocking filter to a fundus camera.

The broadband white light source employs a xenon flash tube or a xenon light bulb, which has a spectrum over a wide band including an ultraviolet band, a visible band, and a near infrared band, as a light source. Since there are many types of general camera-type fluorescent fundus angiography devices in which a color fundus camera function is added to fluorescein fluorescent fundus angiography devices, a white xenon flash tube or a white light bulb should be used as a light source.

However, a contrast system employing a broadband white xenon flash tube or bulb has the following disadvantages.

1) Since an on/off response time is very long, high-speed fluorescence fundus angiography cannot be performed.

Since a maximum movement speed of arterial blood perfused to a retinal artery is about 10 cm/s, it is necessary to acquire images of at least 30 frames/second (fps) or more so as to confirm propagation of fluorescence along the blood vessels in an arterial phase of a fluorescence fundus imaging. However, a device performing the above requirement cannot be implemented in the fluorescent fundus angiography device using the above contrast. Thus, since the movement of the contrast medium propagating to the artery cannot be confirmed in real time, there is a disadvantage in that it is difficult to accurately calculate a blood flow rate or to accurately know an exact starting point of the arterial phase. Such a disadvantage has a limitation in accurately measuring an arteriovenous circulation time in a retinal blood vessel, which is an index required to determine diabetic retinopathy, central retinal vein occlusion, and ocular ischemia syndrome.

2) In order for driving the contrast system, a great deal of instantaneous current is required.

In order to drive the flash tube or the light bulb, a great deal of instantaneous current is required. A great deal of power is required for instantaneous driving, and a significant variation in current within a short time generates electrical noise and thus an additional electronic circuit is required to prevent the electrical noise. The significant instantaneous driving current and the noise canceling circuit increase an area of the contrast system, and thus there is a disadvantage of increasing costs. In addition, it is difficult to implement the contrast system as a portable device so that there is a limitation in use of the contrast system in other places in addition to an ophthalmic examination room.

3) A lifetime of the contrast system is short and a replacement cost thereof is high.

The contrast system has disadvantages in that the lifetime of the above light sources is shorter than service lives of a light-emitting diode (LED) and a laser, a replacement cycle is short and frequent, and a price is higher than a price of the LED or a low-power diode laser.

4) Since various spectra are emitted over an entire band, band separation of a filter which excites and blocks a fluorescent material should be thoroughly performed so as to obtain desired performance.

An intensity of fluorescence emitted after the fluorescent material absorbs high-energy light is weak. In order to detect only pure fluorescence emitted from the fluorescent material, it is important to completely block the high-energy light which excited the fluorescent material so as to obtain a high-contrast fluorescent fundus photograph. The illumination system emits various spectra over the entire band and emits not only high-energy waves which excite the fluorescent material, but also waves in a low-energy wavelength band emitted from the fluorescent material, thereby causing a disturbance (a problem of not knowing whether light detected by an imaging system is emitted from the fluorescent material or the illumination system). The light which is a cause of the disturbance is referred to as pseudofluorescence. In order to solve the pseudofluorescence problem, a high-performance bandpass filter in which a passband of the excitation filter and a passband of the blocking filter should be thoroughly separated is required. The price of such a filter is not cheap and contributes to raising the price of a camera-type fluorescent fundus angiography device which employs a white light source.

SUMMARY

The present invention is directed to providing a fluorescent fundus angiography apparatus which employs a light source for emitting light in a narrow spectrum band as an excitation light source and allows a fast response time, a long lifetime, and low current consumption.

The present invention is also directed to providing a fluorescent fundus angiography device which allows high-speed fluorescence fundus angiography with a fast response time and is capable of measuring a movement speed of a fluorescent material which is imaged in the arteries and veins of the retina in real time.

The technical problems to be solved by the present invention are not limited to the above-mentioned technical problems and other technical problems which are not mentioned can be clearly understood by those skilled in the art to which the present invention pertains from the following description.

One aspect of the present invention provides a fluorescent fundus angiography device, which employs a polarizing beam splitter and a linear polarizing filter and observes the retina using fluorescein as a contrast medium, including an excitation light source (10) which is a blue light source having a center wavelength ranging from 470 nm to 490 nm; a diffusion lens (20) configured to diffuse the light incident from the excitation light source (10); an illumination lens (30) configured to irradiate the light incident from the diffusion lens (20) at a predetermined exit angle; a mirror (40) configured to reflect the light incident from the illumination lens (30); a polarizing beam splitter (50) configured to reflect P-polarized light among the light incident from the mirror (40) to an objective lens (60) and allow S-polarized light of light incident from the mirror (40) to pass therethrough; the objective lens (60) configured to enlarge an image of the fundus, which is formed by the light incident from the polarizing beam splitter (50); a short-distance ocular lens (70) configured to reduce or enlarge the image of the fundus, which is enlarged by the objective lens (60); a linear polarizing filter (80) configured to allow only the P-polarized light returning from the fundus to pass therethrough or transmit only the P-polarized light to the fundus; a light blocking filter (90) having a full width at half maximum (FWHM) ranging from 40 nm to 50 nm and configured to filter light having a center wavelength ranging 520 nm to 530 nm or block light having a wavelength that is shorter than 500 nm; an imaging element (100) having an absorption spectrum of light having a center wavelength that is longer than 500 nm using the light passing through the light blocking filter (90); and an excitation filter (110) having an FWHM of 40 nm or less and a center wavelength of 480 nm.

In accordance with the present invention, a fluorescent fundus angiography apparatus which employs a light source for emitting light in a spectrum band that is narrower than a spectrum band of a white light source as an excitation light source and allows a fast response time, a long lifetime, and low current consumption can be provided In addition, in accordance with the present invention, high-speed fluorescence fundus angiography is possible at a fast response time and it is possible to measure a movement speed of a fluorescent material which is imaged in the arteries and veins of the retina in real time.

In addition, in accordance with the present invention, a further clearer image can be obtained by removing various types of internal reflections using a combination of a polarizing beam splitter and a linear polarizing filter in the fundus camera using coaxial illumination.

In addition, in accordance with the present invention, a color fundus camera and a fluorescein fundus angiography device can be simultaneously implemented as one optical platform by adding excitation illumination and excitation filters at an inexpensive price.

In addition, in accordance with the present invention, a high-speed fluorescent fundus photograph is acquired using low contrast energy such that a diagnostic value of the device can be increased. In particular, the present invention is useful for determining a lesion with a reduced blood flow rate, neovascularization such as wet age-related macular degeneration, and a blocked lesion in retinal diseases such as diabetic retinopathy, retinal artery occlusion, and retinal vein occlusion.

In addition, it is possible to photograph a clear fluorescent fundus at a wide angle without addition of an expensive optical device or an expensive laser-based contrast device.

DETAILED DESCRIPTION

The present invention is a fluorescent fundus camera, which is one kind of ophthalmological diagnostic equipment, using a blue excitation light beam when a contrast medium appears in the retinal vessels. When an abnormal blood vessel is present, the contrast medium leaks into the retina or appears as color in tissues surrounding the retina, and the presence of damage to the retina and the appearance of abnormal neovascularization can be found.

Specific matters, including the above problems to be solved, means for solving the problems, and effects of the present invention, are included in the embodiments, which will be described below, and the accompanying drawings. Advantages and features of the present invention and methods for achieving them will be made clear from embodiments described in detail below with reference to the accompanying drawings.

Figure 1:
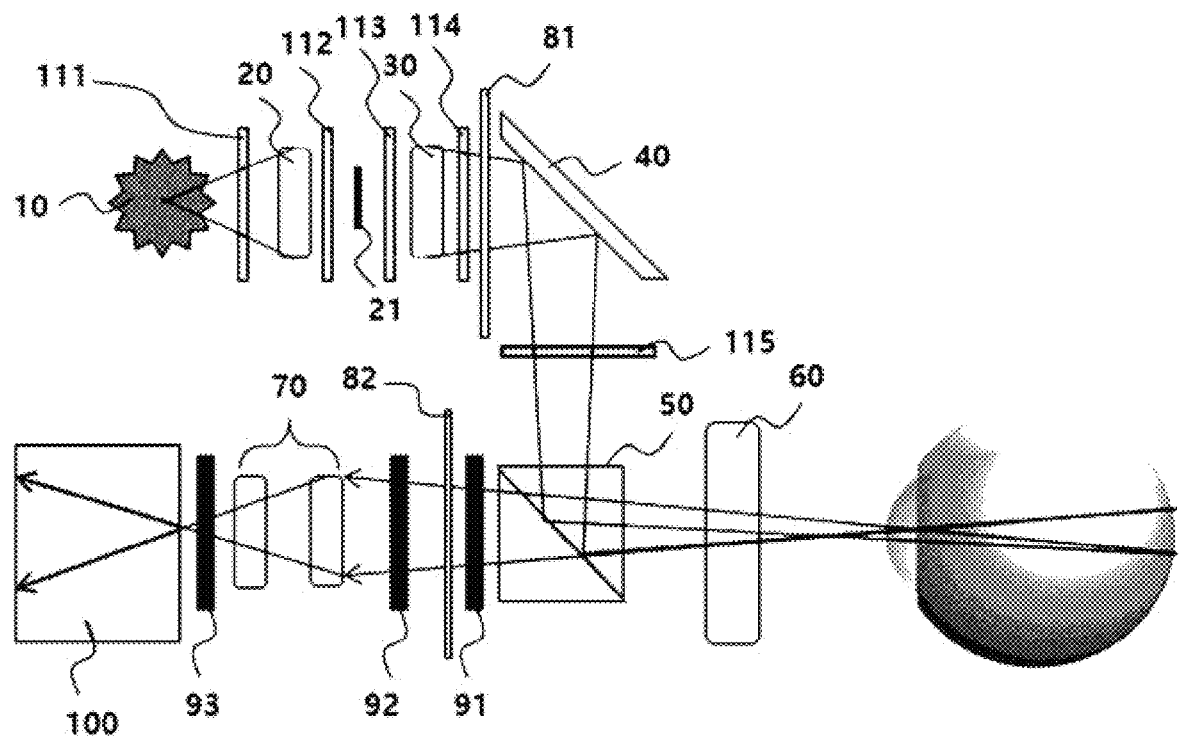
FIG. 1 is a diagram illustrating a configuration of a fluorescein fluorescent fundus angiography device which includes an excitation light source, a light blocking filter, and an excitation filter and employs a polarizing beam splitter and a linear polarizing filter according to the present invention.

As shown in FIG. 1, a fluorescein fluorescent fundus angiography device employing a polarizing beam splitter and a linear polarizing filter according to the present invention is characterized in that components such as a light source 10, a diffusion lens 20, an illumination lens 30, a mirror 40, a polarizing beam splitter 50, an objective lens 60, a short-distance ocular lens 70, a linear polarizing filter 80, a light blocking filter 90, an excitation filter 110, and an imaging element 100 are included in a fluorescent fundus angiography device which observes the retina using fluorescein as a contrast medium.

First, in the fluorescent fundus angiography device according to the present invention, fluorescein is used as a contrast medium. Fluorescein, which is one kind of fluorescent contrast medium, is a fluorescent material which emits green waves having a wavelength ranging from 500 nm to 600 nm when absorbing blue waves having a wavelength ranging from 470 nm to 510 nm. At a typical test concentration, it is known that a maximum absorption wavelength of a fluorescent contrast medium dissolved in plasma is 480 nm and a maximum emission wavelength thereof is 525 nm.

As described in the Background, the core of a general camera-type fluorescent fundus angiography device is formed by adding a broadband white light source, an excitation filter, and a blocking filter to a fundus camera. Since there are many types of general camera-type fluorescent fundus angiography devices in which a color fundus camera function is added to fluorescein fluorescent fundus angiography devices, a white xenon flash tube or a white light bulb should be used as a light source. A contrast system employing a broadband white xenon flash tube or bulb has a problem in that, since an on/off response time is very long, high-speed fluorescence fundus angiography cannot be performed, and a great deal of current is required for driving the contrast system, and thus a lot of noise is generated and costs are increased. In addition, unlike the present invention, there are problems in that a lifetime is short and a replacement cost is high, and, since various spectra are emitted over an entire band, band separation of a filter which excites and blocks a fluorescent material should be thoroughly performed so as to obtain desired performance.

Therefore, the present invention is proposed to solving the above problems using fluorescein which is a fluorescent material which emits green waves having a wavelength ranging from 500 nm to 600 nm when absorbing blue waves having a wavelength ranging from 470 nm to 510 nm.

Next, it is preferable that the light source 10 is a blue light source having a center wavelength of 480 nm.

More specifically, all types of lasers such as light-emitting diodes, laser diodes, solid state lasers, and dye lasers, which have a 480 nm wavelength as a center wavelength, may be used as the light source 10. In addition, the center frequency may be varied from 470 nm to 490 nm, and all the above types of light-emitting diodes (LEDs) or lasers within the above wavelength range may be used as a narrowband excitation light source.

Unlike the laser, the LED has an emission spectrum around the center frequency. Generally, various types of LEDs include LEDs having relatively wide emission spectra ranging from +50 nm to −50 nm around the center frequency and LEDs having relatively narrow emission spectra ranging from +10 nm to −10 nm. All types of these LEDs may be used as narrowband excitation light sources. The LED having a relatively wide emission spectrum ranging from +50 nm to −50 nm has an advantage of being inexpensive. However, the LED has disadvantages in that, as an emission spectrum band becomes wider, an emitted waves having a short wavelength induces autofluorescence of the crystalline lens to reduce contrast of fluorescence fundus photography, and an emitted waves having a long wavelength overlaps a band of the blocking filter and causes pseudofluorescence to reduce the contrast of the fluorescence fundus photography. On the other hand, there is an advantage in that the contrast increases as an emission spectrum is relatively narrow, ranging from +10 nm to −10 nm, but there is a disadvantage in that the price is high. The present invention has a feature in that, since the light source 10 employs a blue light source having a center wavelength of 480 nm, a photograph is photographed with high contrast even when an output of the light source 10 is smaller than an output of the broadband white light source.

According to the present invention, a light source emitting light in a narrow spectrum band is employed as the excitation light source 10 so that effects of a fast response time, a long lifetime, and low current consumption may be obtained.

Next, the diffusion lens 20 diffuses the light incident from the light source 10. Since the diffusion lens 20 includes an imaging mask 21, light may be controlled by the imaging mask 21. The imaging mask 21 suppresses excitation light reflected from the cornea and the crystalline lens.

Next, the illumination lens 30 irradiates the light incident from the diffusion lens 20 at a predetermined exit angle. Owing to the illumination lens 30, the light incident from the diffusion lens 20 is allowed to exit more clearly and uniformly.

Next, the mirror 40 reflects the light incident from the illumination lens 30. The mirror changes a direction of the light incident from the illumination lens 30 to allow the light to exit and go to the polarizing beam splitter 50 which will described below.

When the polarizing beam splitter 50 is employed, a high quality image may be obtained even when an output of a light source is lower than an output of a light source when a non-polarizing beam splitter is employed. Like the fundus camera using the polarizing beam splitter 50, even a fundus camera or a fluorescent fundus camera using a non-polarizing beam splitter should employ the linear polarizing filter 80 so as to reduce corneal reflection and crystalline lens reflection. Since the non-polarizing beam splitter transmits only 50% or less of an output of an incident beam to an objective lens and transmits only 50% or less of a signal returning from the retina to a detector, a magnitude of the signal reaching the detector is very small. On the other hand, the polarizing beam splitter 50 transmits most of incident beams (90% or more) having the same polarization (P wave) to an objective lens and transmits 90% or more of a signal, whose phase is shifted in the retina, transmitted as a P wave to the detector so that optical efficiency is increased.

Figure 9:
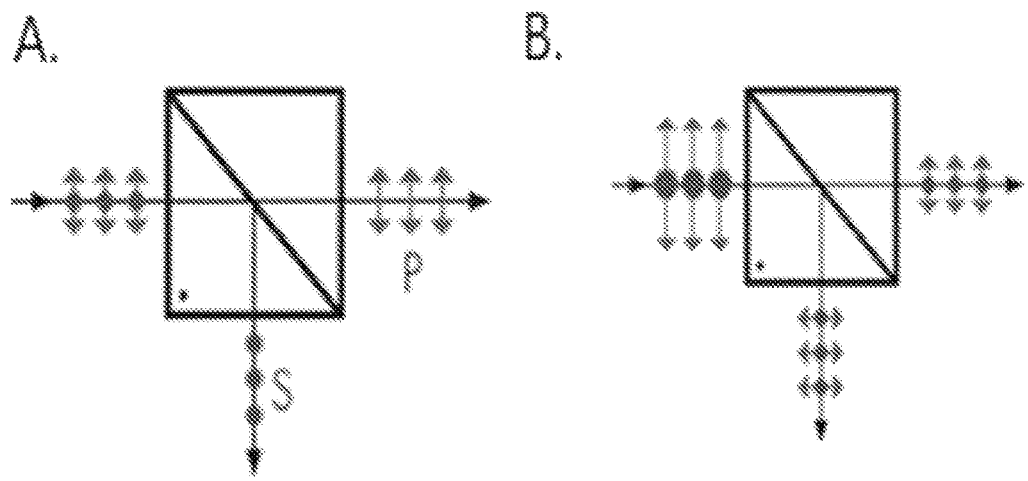
FIG. 9 shows a diagram illustrating the principle (see A) of a polarizing beam splitter (50) and a diagram illustrating the principle (see B) of a non-polarizing beam splitter (50).

More specifically, as shown in FIG. 9, A, all light sources 10 are mixed with light sources corresponding to P-polarized light and light sources 10 corresponding to S-polarized light. In the light source 10, light corresponding to the P-polarized light passes through the polarizing beam splitter 50, and the light corresponding to the S-polarized light is reflected to a portion bent at 90 degrees with respect to an the optical axis due to the polarizing beam splitter 50. Meanwhile, as shown in FIG. 9, B, the same principle as the polarizing beam splitter 50 is not applied to the non-polarizing beam splitter.

Next, the linear polarizing filter 80 is provided in a linear form and filters excitation light to allow only the P-polarized light to pass therethrough before the excitation light reaches the polarizing beam splitter 50. More specifically, it is preferable that the linear polarizing filter 80 is provided to allow the P-polarized light to maximally pass through the polarizing beam splitter 50 and thus allow only pure light polarized in a P-pole direction to pass.

The linear polarizing filter 80 includes a first linear polarizing filter 81 and a second linear polarizing filter 82.

The first linear polarizing filter 81 is provided between the light source 10 and the polarizing beam splitter 50. As the first linear polarizing filter 81 is closer to the light source 10, a size of the first linear polarizing filter 81 may be reduced, and a total cost of the fundus camera manufactured according to the present invention may be reduced.

As shown in FIG. 1, the first linear polarizing filter 81 may be provided between the illumination lens 30 and the mirror 40. When the first linear polarizing filter 81 is provided between the illumination lens 30 and the mirror 40, it is preferable that the first linear polarizing filter 81 is installed to allow only S-polarized light to be incident on the mirror 40 so that P-polarized light whose phase is shifted by 90 degrees due to the mirror 40 is incident on the polarizing beam splitter 50 and the P-polarized light is allowed to be maximally transmitted to the objective lens 60.

In addition, as shown in FIG. 1, the first linear polarizing filter 81 may be provided between the mirror 40 and the polarizing beam splitter 50. When the first linear polarizing filter 81 is provided between the mirror 40 and the polarizing beam splitter 50, it is preferable that the first linear polarizing filter 81 is installed to allow only the P-polarized light to be incident on the polarizing beam splitter 50 so that the P-polarized light is allowed to be maximally transmitted to the objective lens 60.

The second linear polarizing filter 82 is provided between the polarizing beam splitter 50 and the short-distance ocular lens 70. As a distance between the second linear polarizing filter 82 and the polarizing beam splitter 50 is increased, a size of the second linear polarizing filter 82 may be reduced. However, as the distance therebetween is increased, there is a disadvantage in that an overall optical path of the fundus camera manufactured according to the present invention is increased so that a length of the fundus camera is increased.

As shown in the principle of the polarizing beam splitter 50 in FIG. 9, A, when the first linear polarizing filter 81 is located in front of the polarizing beam splitter 50 and then located to allow only light corresponding to the P-polarized light to pass, the retina is irradiated with the largest quantity of light. When the first linear polarizing filter 81 is located to allow only light corresponding to the S-polarized light to pass, the light emitted to the retina is blocked. Therefore, the first linear polarizing filter 81 is a device for controlling the quantity of light and also serves to allow the fundus to be irradiated with only pure P-polarized light.

In addition, when the P-polarized light passing through the polarizing beam splitter 50 is reflected and returned due to an optical medium in front of the polarizing beam splitter 50, the P-polarized light is changed into S-polarized light according to the principle in which, when light is reflected, a phase thereof is shifted to 180° and thus P-polarized light is changed into S-polarized light. The light changed into the S-polarized light is reflected at an angle of 90° due to the polarizing beam splitter 50 such that the S-polarized light cannot be incident on the detector. Similarly, a portion of the light, which is irradiated as P-polarized light while being diffuse-reflected in various paths in the retina, retinal pigment epithelium, and choroid, which are optical media, is reflected as S-polarized light, and the remaining portion of the light is reflected as P-polarized light such that only the P-polarized light passes through the polarizing beam splitter 50.

The P-polarized light passing through the polarizing beam splitter 50 passes through the second linear polarizing filter 82 such that only a high-purity P-polarized retina image is transmitted to the detector, and noise due to various reflections may be blocked with a high removal rate.

For the purpose of fluorescence fundus imaging, a passband of the second linear polarizing filter 82 may include a band of a blocking filter. When a fluorescent fundus imaging function is added to a color fundus camera, the second linear polarizing filter 82 may include 500 nm, which is the shortest wavelength of the band of the blocking filter, and may include 700 nm, which is an end portion of a band of visible light. When a near-infrared fundus imaging function is included in the color fundus camera, a linear polarizing filter 80 having a passband ranging up to 1000 nm may be used.

Next, the objective lens 60 enlarges an image in which an interior of the fundus is formed after the light incident from the polarizing beam splitter 50 is incident on the fundus.

Next, the short-distance ocular lens 70 reduces or enlarges the image of the fundus enlarged by the objective lens 60, and a user checks or detects the image of the fundus.

Next, the light blocking filter 90 is a component which should be essentially used in the present invention. As the light blocking filter 90, a band pass filter which filters light having a center wavelength ranging from 520 nm to 530 nm, or a high frequency blocking filter (or a low pass filter) which blocks light having a wavelength that is shorter than 500 nm is employed. The light blocking filter 90 may be disposed on all surfaces starting from an immediate rear surface of the polarizing beam splitter 50 to a front surface of an imaging sensor on an imaging axis of the fundus camera. A size of the light blocking filter 90 may be reduced by arranging the light blocking filter 90 at a position at which a beam width of the fundus image is geometrically optically minimized so that a system cost may be reduced.

However, the position of the light blocking filter 90 is not important in terms of image quality.

For the purpose of only fluorescence fundus imaging, it is preferable that a full width at half maximum (FWHM) ranges from 40 nm to 50 nm. When the FWHM exceeds or is wider than 50 nm, there are advantages in that the price is low and more energy may be obtained. However, there are disadvantages in that an objective lens 60 having a small aberration should be used so as to compensate for chromatic aberration in a wide frequency band, and the band of the excitation light source 10 is included so that contrast is degraded due to pseudofluorescence. However, when the fundus camera includes a function of fluorescence fundus imaging, since the chromatic aberration of the objective lens 60 is corrected in the band of visible light band, the chromatic aberration correction capability of the objective lens 60 is not important.

In addition, when an FWHM of the light blocking filter 90 is narrow, there are advantages in that the objective lens 60 having a relatively large chromatic aberration may be used, a price of the objective lens 60 becomes low, and the possibility of pseudofluorescence occurring is reduced due to further separation from the excitation wavelength such that it is possible to acquire an image of higher quality. However, when the FWHM of the light blocking filter 90 is less than 40 nm, there is disadvantage in that energy of the light passing through the blocking filter is reduced, and an exposure time of the image is prolonged due to less energy such that time resolution of the fluorescence fundus imaging is reduced, and it has disadvantage of an increased cost due to use of a more sensitive imaging sensor. Therefore, it is preferable that the FWHM ranges from 40 nm to 50 nm.

The range of the FWHM should be adjusted by the band of the excitation light source 10. When the excitation light source 10 is a light source including a band of 500 nm or more, the FWHM should be 50 nm or less so as to reduce pseudofluorescence and increase the contrast of an image. Otherwise, a portion of the excitation light emitted after the retina is irradiated with the light of the excitation light source 10 passes through the blocking filter so that the contrast is reduced. In addition, when the excitation light source 10 is a narrowband light source for emitting only light of 500 nm or less, the FWHM of 50 nm is suitable, and when the excitation light source 10 of several nm is employed as narrow as a laser light source, the FWHM may be further increased. That is, an emission width of the excitation light source 10 and the FWHM of the blocking filter are in a trade-off relationship. In consideration that a maximum absorption wavelength of fluorescein is 480 nm and a maximum emission wavelength is 525 nm, an example of an efficient system design is to use a blocking filter having an FWHM of 45 nm which is a difference between the maximum absorption wavelength and the maximum emission wavelength and use the excitation light source 10 having a bandwidth of 45 nm based on a center wavelength of 480 nm.

Figure 2:
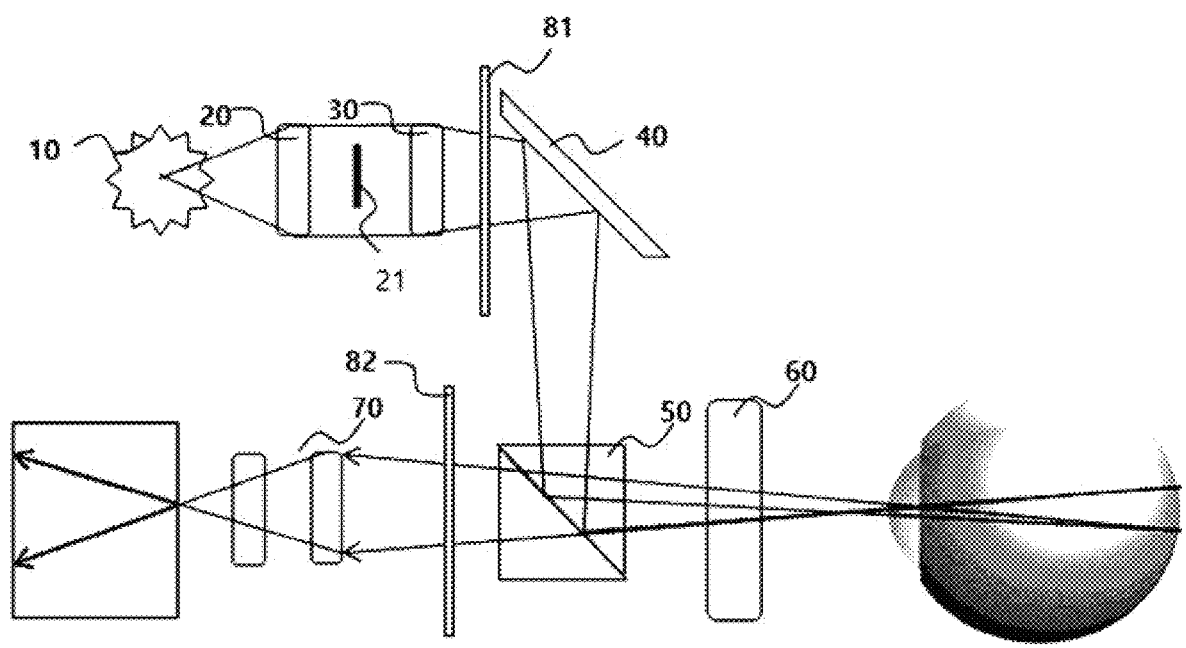
FIG. 2 is a diagram illustrating a conventional fundus camera manufactured with a configuration of a linear polarizing filter and a polarizing beam splitter without employing the excitation light source, the light blocking filter, and the excitation filter.

As in the configuration of FIG. 2, even the fundus camera including the polarizing beam splitter 50 and the two linear polarizing filters 80 without the light blocking filter 90 may remove various noises reflected from other places instead of the retina and capture a clear retinal image.

The light blocking filter 90 includes a first light blocking filter 91, a second light blocking filter 92, and a third light blocking filter 93. The light blocking filter 90 may be provided anywhere between the polarizing beam splitter 50 and the imaging element 100. Since chromatic aberration occurs due to a difference in refractive index according to a wavelength of the light generated from the light source 10, it is preferable to reduce the generation of noise by allowing only a narrow spectrum to pass using the light blocking filter 90. The light blocking filter 90 may be provided by selecting one or more among the first light blocking filter 91, the second light blocking filter 92, and the third light blocking filter 93 or selecting all the three filters.

First, the first light blocking filter 91 is provided between the polarizing beam splitter 50 and the second linear polarizing filter 82. The first light blocking filter 91 is provided between the polarizing beam splitter 50 and the second linear polarizing filter 82 such that there is an advantage in that the second linear polarizing filter 82 is attachable to the light blocking filter 90 in the form of a film.

The second light blocking filter 92 is provided between the second linear polarizing filter 82 and the short-distance ocular lens 70. When the second narrowband light filter 92 is inserted between the second linear polarizing filter 82 and the short-distance ocular lens 70, there is an advantage in that the fundus camera may be used as a fluorescent fundus imaging device. When the second narrowband light filter 92 is removed from between the second linear polarizing filter 82 and the short-distance ocular lens 70, there is an advantage in that the fundus camera may be used as a general fundus camera.

The third light blocking filter 93 is provided between the short-distance ocular lens 70 and the imaging element 100. The third light blocking filter 93 is provided between the short-distance ocular lens 70 and the imaging element 100 to minimize optical interference between the light blocking filter 90 and the imaging element 100. When the third light blocking filter 93 is moved, there is an advantage in that the imaging element 100 equipped with a filter case and the like may be used as the fluorescent fundus imaging device and the general fundus camera.

Next, the imaging element 100 converts the light passing through the light blocking filter 90 into an electrical signal to acquire a photographed image. It is preferable that an imaging device having an absorption spectrum of light having a wavelength that is longer than 500 nm is used as the imaging element 100. More preferably, an analog-type charge coupled device (CCD) or a complementary metal oxide semiconductor (CMOS) may be used as the imaging element 100. In addition, it is possible to use either a color imaging element or a mono imaging element, having a built-in Bayer pattern, as the imaging element 100.

Figure 10:
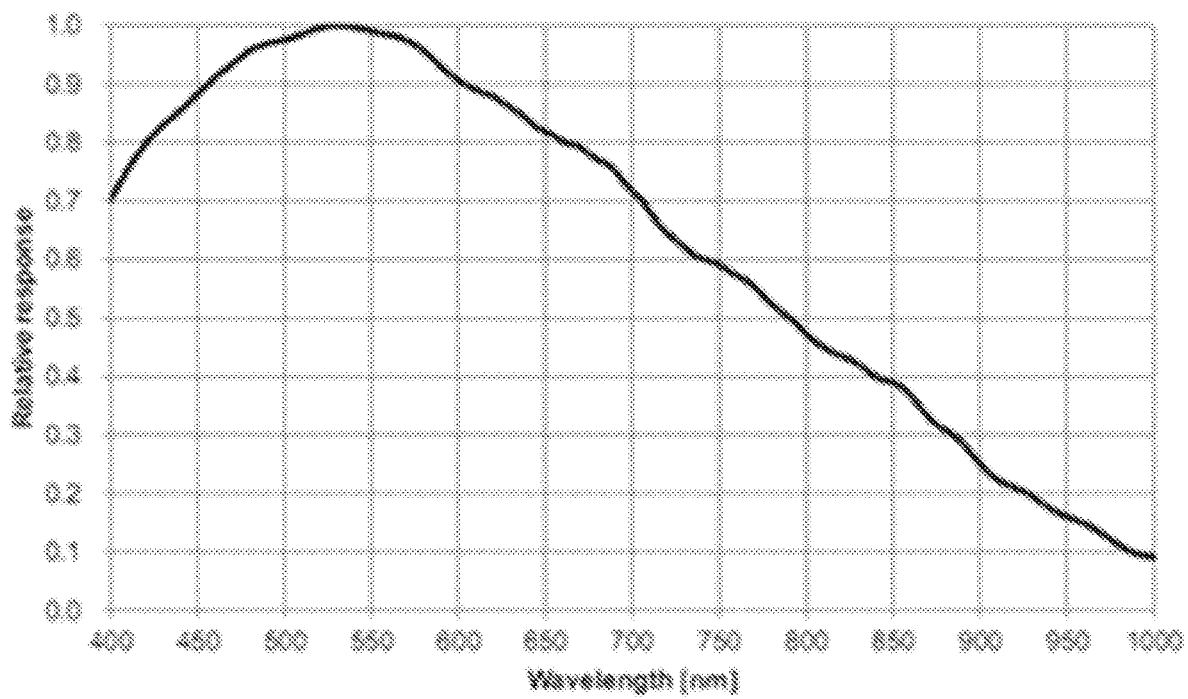
FIG. 10 is a graph showing photon efficiency of a monochrome imaging element (100).

As shown in FIG. 10, the photon efficiency of the commercially available imaging element 100 is drastically reduced with respect to light having a wavelength that is longer than 700 nm and is high with respect to green waves having a wavelength ranging from 500 nm to 600 nm, which is an emission band of fluorescein. Therefore, there is no great difficulty in using the commercially available imaging element 100 as an imaging element for fluorescence fundus imaging.

In addition, the imaging element 100 is provided coaxially with the light source 10 so that there is an advantage of reducing strong light reflected from the cornea, the crystalline lens, the optic nerve papilla, and inner boundary membrane of the retina of a human, and uniformly contrasting the retina.

Next, the excitation filter 110 is preferably provided between the light source 10 and the polarizing beam splitter 50. The excitation filter 110 is a bandpass optical filter having a center wavelength of 480 nm, and all kinds of bandpass optical filters having a FWHM of 40 nm or less may be used as the excitation filter 110. In addition, when a monochromatic light source having a center wavelength different from 480 nm is employed, an excitation filter having a wavelength corresponding to the center wavelength may be used as the excitation filter.

As the FWHM of the excitation filter 110 is narrower, pure light near the center frequency is transmitted to the fundus and is independent from a further lower emission frequency emitted from fluorescein used as the contrast medium, and it is easy to be free of a problem such as pseudofluorescence or autofluorescence of the crystalline lens, which degrades the quality of the fluorescent fundus camera. The excitation filter 110 may increase the contrast of an image but has a disadvantage of being expensive.

On the other hand, when the FWHM of the excitation filter 110 is wide, there is an advantage in that the price is cheap. When a light source having a wide spectrum is employed, more energy may be transferred to fluorescein to obtain a large amount of fluorescence emission energy. However, there is a problem in that image quality is degraded due to pseudofluorescence or autofluorescence of the crystalline lens. Generally, it is most preferable that the FWHM of the excitation filter 110 ranges from 20 nm to 40 nm.

In addition, like the laser light source, the laser diode, and the narrowband LED, a light source having a narrow emission spectrum ranging from +20 nm to −20 nm at a center wavelength of 480 nm to 480 nm does not require the excitation filter 110. Therefore, in this case, there is an advantage in that the system is cheaper by as much as the price of the excitation filter 110. The following description relates to a fluorescein fundus angiography device, in which a narrowband light source having a center wavelength of 480 nm, which is developed based on the above description, the linear polarizing filter 80, and the excitation filter 110 are disposed, implemented and shown in FIG. 3.

Figure 3:
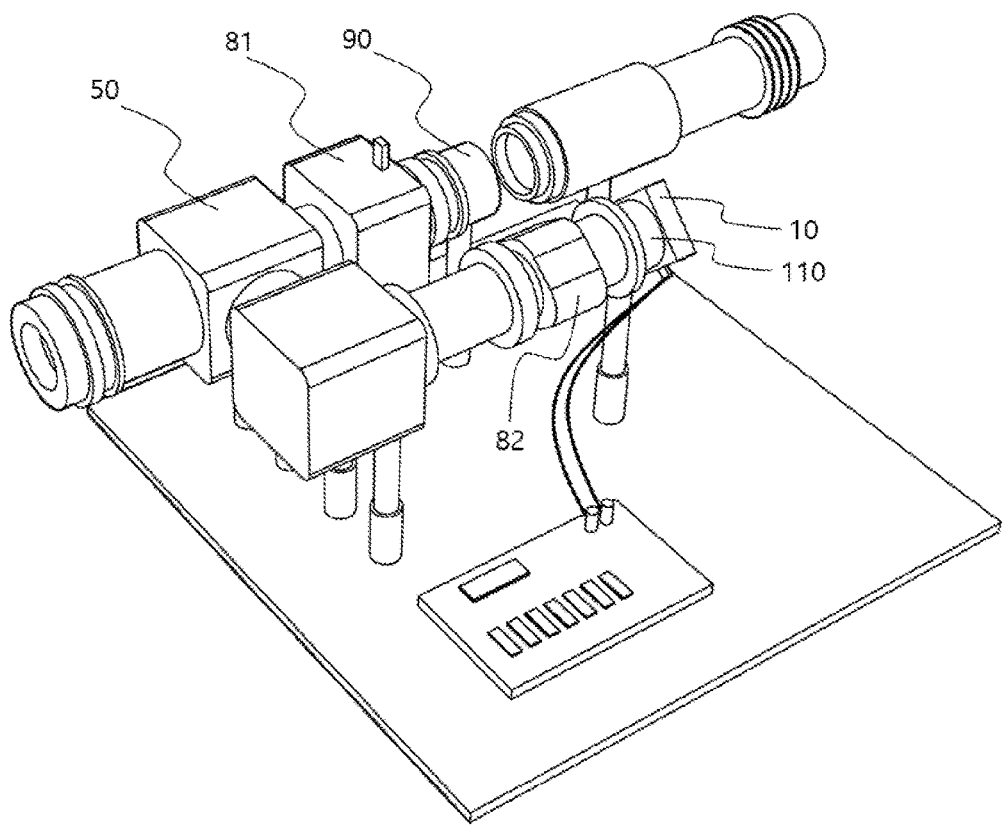
FIG. 3 is a photograph showing an implementation example of a fluorescein fluorescent fundus angiography device which employs a narrowband excitation light source and in which an excitation light source having a 480 nm center wavelength, a light blocking filter, and an excitation filter are disposed according to the present invention.

In FIG. 3, like the fluorescein fundus angiography device in which the light source having a center wavelength of 480 nm, the linear polarizing filter 80, and the excitation filter 110 are disposed, this equipment is implemented by switching illumination from a previously developed color fundus camera and adding the two filters thereto.

Figure 4:
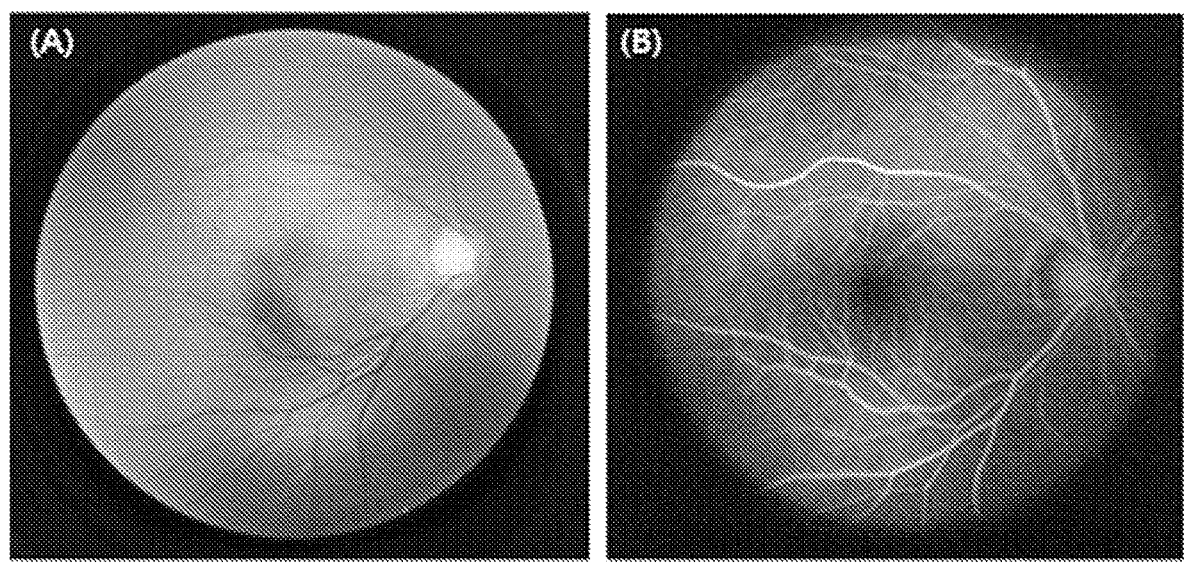
FIG. 4 shows a color fundus photograph (see A) and a fluorescein fluorescent fundus photograph (see B) which are obtained using a basic optical platform.

FIG. 4 shows an image (see A) photographed using the previously developed color fundus camera and an image (see B) photographed using the fluorescent fundus angiography device of the present invention.

Next, the following description relates to fluorescein fluorescent fundus images which are sequentially acquired after intravenous injection of fluorescein through the fluorescein fundus angiography apparatus manufactured according to the present invention, in which the light source having a center wavelength of 480 nm, the linear polarizing filter 80, and the excitation filter 110 are disposed.

Figure 5:
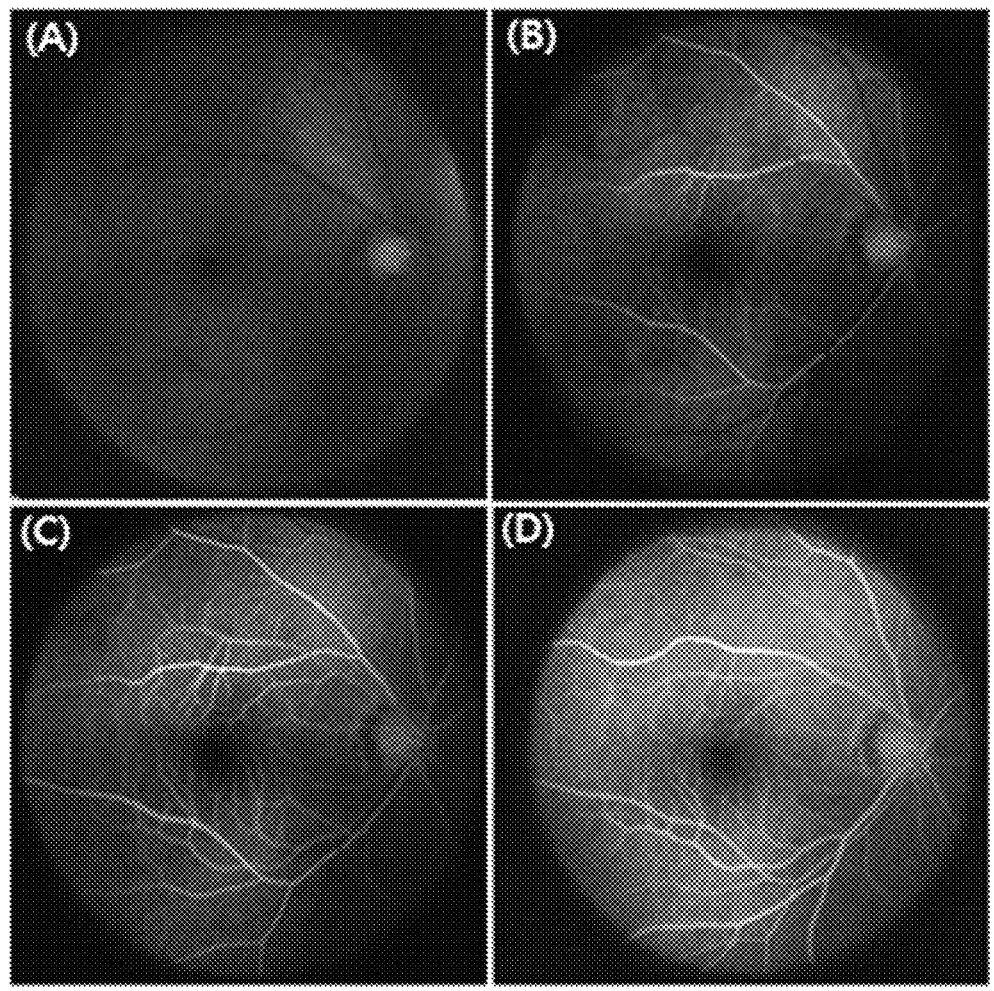
FIG. 5 shows fluorescein fluorescent fundus photographs which are sequentially obtained after intravenous injection of fluorescein through the fluorescein fluorescent fundus angiography device which employs the narrowband excitation light source and in which the excitation light source having the 480 nm center wavelength, the light blocking filter, and the excitation filter are disposed according to the present invention (A is a photograph obtained at a time of nine seconds after choroidal injection, B is a photograph obtained at a time of eleven seconds after arterial injection, C is a photograph obtained at a time of eighteen seconds after arteriovenous injection, and D is a photograph obtained at a time of twenty-five seconds after intravenous injection).

As shown in FIG. 5, the fluorescein fluorescent fundus photographs deliver different image information for each time from a time when the contrast medium is injected into the vein. The sequence starts from about eight seconds which is the time for the fluorescein to reach the heart and the retina after the intravenous injection of fluorescein, and the information may be sequentially obtained in the form of a choroidal stage—an arterial stage—an arteriovenous stage—a venous stage—a recirculation stage—late stage.

FIG. 5, A is a photograph obtained at a time of nine seconds after choroidal injection, FIG. 5, B is a photograph obtained at a time of eleven seconds after arterial injection, FIG. 5, C is a photograph obtained at a time of eighteen seconds after arteriovenous injection, and FIG. 5, D is a photograph obtained at a time of twenty-five seconds after intravenous injection. As shown in FIG. 5, it was possible to perform high-speed fluorescent fundus angiography with a fast response time and measure a movement speed of a fluorescent material which is contrasted in arteries and veins of the retina in real time.

Figure 6:
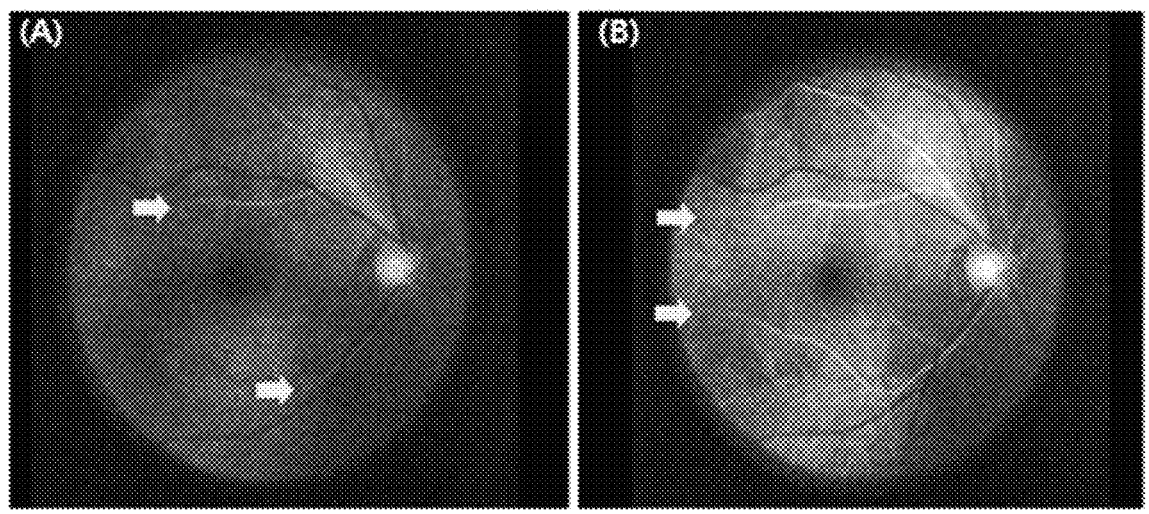
FIG. 6 shows photographs in which a propagation pattern of a fluorescein contrast medium is confirmed in retinal arteries through the fluorescein fluorescent fundus angiography device which employs the narrowband excitation light source and in which the excitation light source having the 480 nm center wavelength, the light blocking filter, and the excitation filter are disposed according to the present invention (A is a photograph obtained at a time of 10.300 seconds in a middle stage after arterial injection, and B is a photograph obtained at a time of 10.550 seconds in a late stage after the arterial injection).

Next, a propagation pattern in retinal arteries of the fluorescein contrast medium was confirmed through the angiography device manufactured according to the present invention. As shown in FIG. 6, by forming a polarized fundus camera including the objective lens 60, the polarizing beam splitter 50, and two linear polarizing filters 80 was formed as a basic optical platform, the fundus was illuminated with further less illumination energy to reduce glare, there was no noise such as corneal reflection and the like, and a loss was small such that a fundus image was acquired using a short exposure. These advantages allow fluorescent fundus imaging at high speed.

FIG. 6, A show a photograph obtained at a time of 10.300 seconds in a middle phase after arterial injection, and FIG. 6, A shows a photograph obtained at a time of 10.550 seconds in a late phase after the arterial injection. When fluorescent fundus imaging is performed using the above equipment, ultra-fast fluorescent fundus imaging corresponding to 200 frames/second is possible in a 1000×1000 pixel CCD having an area of one inch. Referring to FIG. 6, it can be confirmed that the fluorescein contrast medium propagates along the retinal arteries in real time. In addition, a length of a blood vessel is measured by combining the obtained photograph with an ophthalmic tomography image and then the length is divided by a difference in propagation time such that a speed of the contrast medium propagating along the artery may be calculated.

Figure 7:
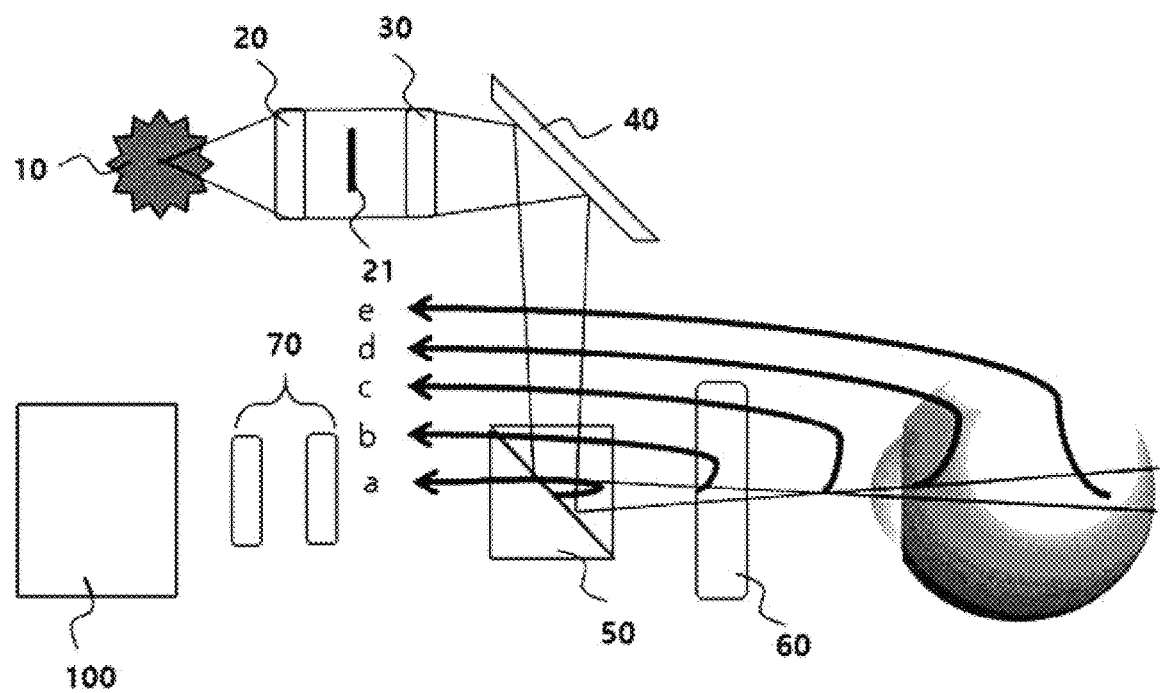
FIG. 7 is a diagram illustrating a configuration of a conventional fundus camera and optical noises (a to e) generated due to components.
Figure 8:
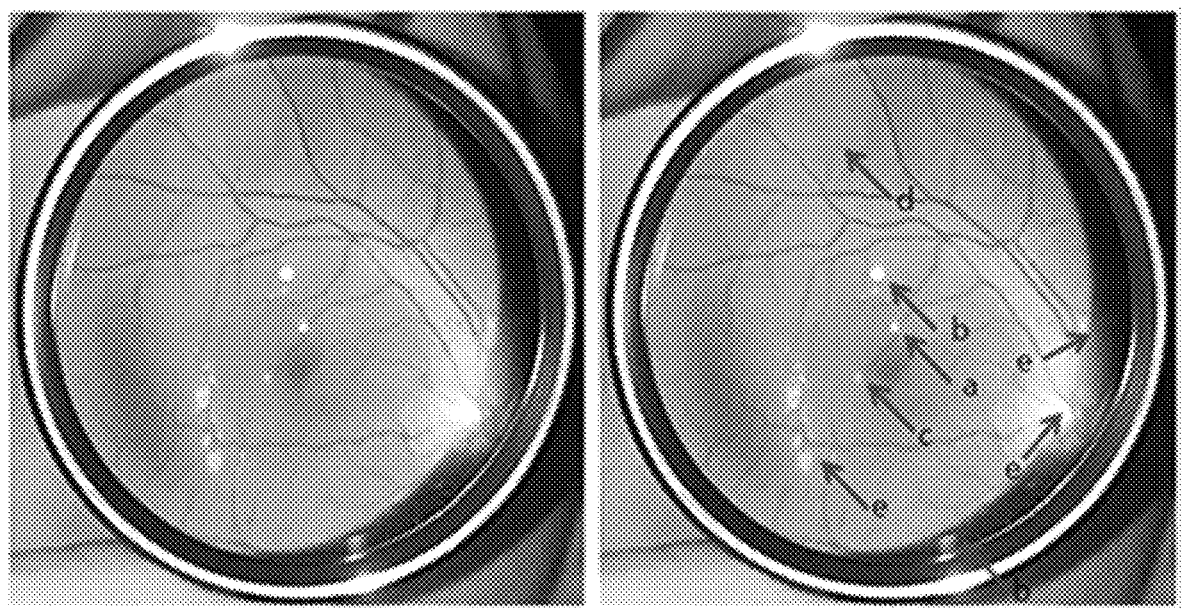
FIG. 8 shows photographs illustrating the optical noises (a to e) which appear when a fundus is photographed using the conventional fundus camera of FIG. 7.

Referring to FIGS. 7 and 8, hereinafter, the problems of a general fundus camera will be identified.

1. Configuration of General Coaxial Illumination Fundus Camera

FIG. 7 shows a basic configuration of a general coaxial illumination fundus camera. As shown in FIG. 7, the polarizing beam splitter 50 is a core component which allows illumination for imaging the fundus to be coaxial with a contrast image of the fundus. However, in the conventional coaxial illumination fundus camera, a great deal of light is lost while the light passes through the polarizing beam splitter 50, and light noise due to various reflections generated in the polarizing beam splitter 50 enters the detector without filtration.

2. Various Light Reflections Generated in General Coaxial Illumination Fundus Camera Red arrows in FIG. 7 indicate causes and problems of various reflections which may be generated in the general coaxial illumination fundus camera. An arrow a indicates a reflection generated in the polarizing beam splitter 50, and an arrow b indicates a reflection due to the objective lens 60. An arrow c indicates a reflection generated due to the cornea. An arrow d indicates a reflection generated due to the crystalline lens. An arrow e indicates total reflections generated due to the vitreous body and the retina. When a fundus photograph is photographed, due to the reflections indicated by the arrows a to e, various reflection patterns appear such that a great deal of confusion creates a hassle for a doctor checking the fundus of a patient.

3. Fundus Photographs Photographed Using General Coaxial Illumination Fundus Camera FIG. 8 shows fundus photographs photographed using the general coaxial illumination fundus camera, and the substance of the reflections indicated by the arrows a to e in FIG. 7 can be confirmed through the fundus photographs. As in FIG. 7, an arrow a indicates a reflection generated in the polarizing beam splitter 50, and an arrow b indicates a reflection due to the objective lens 60. An arrow c indicates a reflection generated due to the cornea. An arrow d indicates a reflection generated due to the crystalline lens. An arrow e indicates total reflections generated due to the vitreous body and the retina. When a position of an eye of the patient is varied or an angle between an optical system and a visual axis is varied, patterns of the reflections indicated by the arrows a to e vary unpredictably so that the variation cannot be removed by software and thus there is a problem of degrading a diagnostic value of the equipment.

According to the present invention, a fluorescent fundus angiography apparatus, which employs a light source for emitting light in a narrow spectrum band as an excitation light source and allows a fast response time, a long lifetime, and low current consumption, may be provided.

In addition, according to the present invention, high-speed fluorescence fundus angiography is possible at a fast response time and it is possible to measure a movement speed of a fluorescent material which is imaged in the arteries and veins of the retina in real time.

In addition, according to the present invention, a further clearer image may be obtained by removing various types of internal reflections using a combination of a polarizing beam splitter and a linear polarizing filter in the fundus camera using coaxial illumination.

In addition, according to the present invention, a color fundus camera and a fluorescein fundus angiography device may be simultaneously implemented as one optical platform by adding illumination and filters at an inexpensive price.

In addition, according to the present invention, a high-speed fluorescent fundus photograph is acquired using low contrast energy such that a diagnostic value of the device may be increased. In particular, the present invention is useful for determining a lesion with a reduced blood flow rate, neovascularization, and a blocked lesion in retinal diseases such as diabetic retinopathy, macular degeneration, retinal artery occlusion, and retinal vein occlusion.

In addition, it is possible to photograph a fluorescent fundus at a wide angle without addition of an expensive optical device or an expensive laser-based contrast device.

As described above, it will be understood that the above described technical configuration of the present invention can be implemented in other specific forms without changing the technical spirit or essential features of the present invention by those skilled in the art.

Therefore, it should be understood that the above described embodiments are not restrictive but illustrative in all aspects, and the scope of the present invention is defined by the appended claims rather than the detailed description, and it should be construed that all changes or modifications derived from the meaning and scope of the appended claims and the equivalents thereof fall within the scope of the present invention.

The invention claimed is:

1. A fundus angiography device employing a polarizing beam splitter and a linear polarizing filter, comprising:
    a light source (10) which is a blue light source having a center wavelength ranging from 470 nm to 490 nm;
    a diffusion lens (20) configured to diffuse the light incident from the light source (10);
    an illumination lens (30) configured to irradiate the light incident from the diffusion lens (20) at a predetermined exit angle;
    a mirror (40) configured to reflect the light incident from the illumination lens (30);
    a polarizing beam splitter (50) configured to allow P-polarized light of the light incident from the mirror (40) to pass therethrough and reflect S-polarized light among light incident from the mirror (40);
    an objective lens (60) configured to enlarge an image of the fundus which is formed by the light incident from the polarizing beam splitter (50);
    a short-distance ocular lens (70) configured to reduce or enlarge the image of the fundus which is enlarged by the objective lens (60);
    a linear polarizing filter (80) configured to allow only the P-polarized light to pass therethrough;
    a light blocking filter (90) configured to filter light having a center wavelength ranging from 520 nm to 530 nm or block light having a wavelength that is shorter than 500 nm among the light passing through the linear polarizing filter (80);
    an excitation filter (110) provided between the light source (10) and the polarizing beam splitter (50) and having a center wavelength of 480 nm; and
    an imaging element (100) configured to convert the light passing through the light blocking filter (90) into an electrical signal,
    wherein the linear polarizing filter (80) includes a first linear polarizing filter (81) provided between the light source (10) and the polarizing beam splitter (50), and a second linear polarizing filter (82) provided between the polarizing beam splitter (50) and the short-distance ocular lens (70).

2. The fundus angiography device of claim 1, wherein the linear polarizing filter (90) includes one or more among a first light blocking filter (91) provided between the polarizing beam splitter (50) and the second linear polarizing filter (82), a second light blocking filter (92) provided between the second linear polarizing filter (82) and the short-distance ocular lens (70), and a third light blocking filter (93) provided between the short-distance ocular lens (70) and the imaging element (100).

3. The fundus angiography device of claim 1, wherein the linear polarizing filter (90) has a full width at half maximum (FWHM) ranging from 40 nm to 50 nm.

4. The fundus angiography device of claim 1, wherein the excitation filter has a full width at half maximum (FWHM) of 40 nm or less.

5. The fundus angiography device of claim 1, wherein the excitation filter is a bandpass optical filter.

* * * * *